US010813941B2

(12) United States Patent
Dowd et al.

(10) Patent No.: US 10,813,941 B2
(45) Date of Patent: Oct. 27, 2020

(54) METHODS AND COMPOUNDS FOR TREATING MALARIA (71) Applicants: THE GEORGE WASHINGTON UNIVERSITY, A CONGRESSIONALLY CHARTERED NOT-FOR-PROFIT CORPORATION, Washington, DC (US); WASHINGTON UNIVERSITY IN ST. LOUIS, St. Louis, MO (US)

(72) Inventors: Cynthia Dowd, Washington, DC (US); Audrey Odom, St. Louis, MO (US); Rachel Edwards, St. Louis, MO (US); Robert Brothers, Washington, DC (US)

(73) Assignees: The George Washington University, A Congressionally Chartered Not-For-Profit Corporation, Washington, DC (US); Washington University in St. Louis, St. Louis, MO (US)

( * ) Notice: Subject to any disclaimer, the term of this patent is extended or adjusted under 35 U.S.C. 154(b) by 0 days.

(21) Appl. No.: 16/071,459

(22) PCT Filed: Jan. 23, 2017

(86) PCT No.: PCT/US2017/014564
§ 371 (c)(1),
(2) Date: Jul. 19, 2018

(87) PCT Pub. No.: WO2017/127805
PCT Pub. Date: Jul. 27, 2017

(65) Prior Publication Data
US 2019/0030056 A1    Jan. 31, 2019

Related U.S. Application Data (60) Provisional application No. 62/281,969, filed on Jan. 22, 2016.

(51) Int. Cl.
| | |
|---|---|
| *A61K 31/7056* | (2006.01) |
| *A61K 45/06* | (2006.01) |
| *A61K 31/122* | (2006.01) |
| *A61K 31/137* | (2006.01) |
| *A61K 31/357* | (2006.01) |
| *A61K 31/366* | (2006.01) |
| *A61K 31/437* | (2006.01) |
| *A61K 31/4706* | (2006.01) |
| *A61K 31/496* | (2006.01) |
| *A61K 31/65* | (2006.01) |
| *A61K 31/49* | (2006.01) |
| *A61K 31/683* | (2006.01) |
| *A61K 31/519* | (2006.01) |
| *A61K 31/155* | (2006.01) |
| *A61P 33/06* | (2006.01) |

(52) U.S. Cl.
CPC ........ *A61K 31/7056* (2013.01); *A61K 31/122* (2013.01); *A61K 31/137* (2013.01); *A61K 31/155* (2013.01); *A61K 31/357* (2013.01); *A61K 31/366* (2013.01); *A61K 31/437* (2013.01); *A61K 31/4706* (2013.01); *A61K 31/49* (2013.01); *A61K 31/496* (2013.01); *A61K 31/519* (2013.01); *A61K 31/65* (2013.01); *A61K 31/683* (2013.01); *A61K 45/06* (2013.01); *A61P 33/06* (2018.01); *Y02A 50/411* (2018.01)

(58) Field of Classification Search
CPC .. A61K 31/122; A61K 31/137; A61K 31/155; A61K 31/357; A61K 31/366; A61K 31/437; A61K 31/4706; A61K 31/49; A61K 31/496; A61K 31/519; A61K 31/65; A61K 31/683; A61K 31/7056; A61K 45/06; A61P 33/06; Y02A 50/411
See application file for complete search history.

(56) References Cited

U.S. PATENT DOCUMENTS

| | | | |
|---|---|---|---|
| 9,593,136 B2 * | 3/2017 | Boshoff | ................ A01N 57/18 |
| 2008/0312190 A1 | 12/2008 | Van Calenbergh et al. | |
| 2014/0378418 A1 | 12/2014 | Boshoff et al. | |
| 2015/0065466 A1 | 3/2015 | Song | |

FOREIGN PATENT DOCUMENTS

WO    WO-2004019956 A1 *    3/2004    ........... A61K 31/662

OTHER PUBLICATIONS

Uh et al., "Antibacterial and antitubercular activity of fosmidomycin, FR900098, and their lipophilic analogs", 2011, Bioorg. Med. Chem. Lett., 21(23), pp. 6973-6976. (Year: 2011).*

Jackson et al., "The effect of chain length and unsaturation on Mtb Dxr inhibition and antitubercular killing activity of FR900098 analogs", 2014, Bioorg. Med. Chem. Lett., 24(2), pp. 649-653. (Year: 2014).*

Edwards et al., "MEPicides: potent antimalarial prodrugs targeting isoprenoid biosynthesis", 2017,Sci Rep., 7(1):8400 (DOI:10.1038/s41598-017-07159-y), pp. 1-11. (Year: 2017).*

(Continued)

*Primary Examiner* — My-Chau T. Tran
(74) *Attorney, Agent, or Firm* — Venable LLP; Keith G. Haddaway; Miguel A. Lopez (57) ABSTRACT

A pharmaceutical composition includes a small molecule and a pharmaceutically acceptable excipient. The small molecule interacts with a deoxyxylulose phosphate reductoisomerase (Dxr). A method for treating or preventing a microbial infection in a subject in need thereof includes administering the pharmaceutical composition. A method for inhibiting the growth of a eukaryotic pathogen includes contacting the eukaryotic pathogen with an effective amount of the pharmaceutical composition.

14 Claims, 4 Drawing Sheets

(56) References Cited

OTHER PUBLICATIONS

Wang et al., "MEPicides: α,β-Unsaturated Fosmidomycin Analogues as DXR Inhibitors against Malaria", 2018, J. Med. Chem. 2018, 61(19), pp. 8847-8858. (Year: 2018).*

Kuntz et al., "Isoprenoid biosynthesis as a target for antibacterial and antiparasitic drugs: phosphonohydroxamic acids as inhibitors of deoxyxylulose phosphate reducto-isomerase", 2005, Biochem. J., 386(1), pp. 127-135. (Year: 2005).*

Woo et al., "Evaluation of f osmidomycin analogs as inhibitors of the *Synechocystis* sp. PCC6803 1-deoxy-o-xylulose 5-phosphate reductoisonnerase", 2006, Bioorganic & Medicinal Chemistry, 14(7), pp. 2375-2385. (Year: 2006).*

Armstrong et al., "Resistance to the antimicrobial agent fosmidomycin and an FR900098 prodrug through mutations in the deoxyxylulose phosphate reductoisomerase gene (dxr)", Sep. 2015, Antimicrob. Agents Chemother., 59(9), pp. 59:5511-5519 (doi:10.1128/AAC.00602-15). (Year: 2015).*

Jomaa et al., "Inhibitors of the Nonmevalonate Pathway of Isoprenoid Biosynthesis as Antimalarial Drugs", 1999, Science, 285 (5433), pp. 1573-1576. (DOI: 10.1126/science.285.5433.1573) (Year: 1999).*

Wiesner, J. et al., "Double ester prodrugs of FR900098 display enhanced in-vitro antimalarial activity." Arch Pharm Chemistry in Life Sciences, 2007, vol. 340, pp. 667-669.

Guggiberg, AM et al., "A sugar phosphatase regulates the methylerythritol phosphate (MEP) pathway in malaria parasites." Nat Commun, 2014, 5:4467.

Imlay, LS et al, "Isoprenoid metabolism in apicomplexan parasites." Curr Clin Microbiol, 2014, Rep 1(3-4):37-50.

Imlay, LS et al., "Plasmodium IspD (2-C-Methyl-d-erythritol 4-Phosphate Cytidyltransferase), an Essential and Druggable Antimalarial Target." ACS Infect Dis, 2015, 1(4): 157-167.

Jackson ER, et al. "Inhibition of 1-Deoxy-D-xylulose-5-phosphate reductoisomerase (DXR): a review of the synthesis and biological evaluation of recent inhibitors." Curr Top Med Chem, 2012, 12(7):706-728.

Zhang, B. et al. "A second target of the antimalarial and antibacterial agent fosmidomycin revealed by cellular metabolic profiling." Biochemistry, 2011, 50(17): 3570-3577.

* cited by examiner

METHODS AND COMPOUNDS FOR TREATING MALARIA

CROSS-REFERENCE OF RELATED APPLICATION

This application is a U.S. National Stage Application under 35 U.S.C. § 371 of PCT/US2017/014564, filed on Jan. 23, 2017, which in turn claims priority to U.S. Provisional Application No. 62/281,969 filed Jan. 22, 2016; the entire contents of all of which are hereby incorporated by reference.

BACKGROUND

1. Technical Field

The field of the currently claimed embodiments of this invention relates to methods, compounds and pharmaceutical compositions for treating or preventing infection caused by *Plasmodium falciparum* or any related *Plasmodium* species.

2. Discussion of Related Art

Despite intense efforts in drug development and aggressive vector control programs, malaria remains a formidable challenge to public health. According to recent estimates, malaria causes 212 million clinical cases and more than 429,000 deaths each year, predominately in young children living in sub-Saharan Africa. While 5 species of Apicomplexan parasites of the genus *Plasmodium* cause human malaria, *Plasmodium falciparum* is the most deadly. Due to pervasive drug resistance, *P. falciparum* treatment has become increasingly dependent on a single class of compounds, the artemisinins. However, there is substantial evidence to suggest that the effectiveness of artemisinin combination therapies (ACTs) is waning, and as such, global malaria control efforts are threatened. The rapid increase in multidrug-resistant parasites combined with a chronic under-investment in drug discovery has severely limited existing therapies. As only a few new antimalarial agents are in the clinical pipeline, identification of novel drug targets is essential.

The methylerythritol phosphate (MEP) pathway of isoprenoid biosynthesis is an unexploited drug target present in most eubacteria and apicomplexan protozoa. In *P. falciparum*, the MEP pathway enzymes are apicoplast-localized, and data suggest that isoprenoid precursor biosynthesis is the only essential function of the plastid organelle in blood-stage parasites. The pathway begins with the condensation of pyruvate and glyceraldehyde-3-phosphate and then proceeds through a series of enzymatic reactions to produce isopentenyl pyrophosphate (IPP) and dimethylallyl diphosphate (DMAPP), which are used to synthesize downstream products. The enzymes of the MEP pathway are essential, as isoprenoids are required for numerous cellular processes including aerobic respiration, membrane stability, and protein prenylation (Imlay 2014). Importantly, humans employ an alternate route for isoprenoid generation, using instead the mevalonate pathway whose components lack similarity to MEP pathway enzymes. Due to the essentiality of the MEP pathway in *P. falciparum* and the absence of mammalian homologs, compounds that would specifically inhibit enzymes in the pathway are paramount.

The first committed enzyme of the MEP pathway is catalyzed by 1-deoxy-D-xylulose-5-phosphate reductoisomerase (Dxr/IspC; EC 1.1.1.267), and considerable efforts have been made to effectively target the enzyme (Jackson 2012). Dxr catalyzes the reductive isomerization of 1-deoxy-D-xylulose 5-phosphate (DOXP) to 2-C-methyl-D-erythritol 3-phosphate (MEP), using a divalent cation ($Mg^{2+}$, $Mn^{2+}$, or $Co^{2+}$) and NADPH as a cofactor (Masini 2014). Chemical inhibition of Dxr in blood-stage *P. falciparum* depletes cellular MEP metabolites, and ultimately kills the parasites (Zhang 2011). Moreover, genetic disruption of the Dxr locus in *P. falciparum* (PF3D7_1467300) is only feasible if cultures are artificially supplemented with downstream isoprenoids (data not shown). Further, Dxr is druggable, contains a high flux-control coefficient, and is one of only seven antimalarial targets that have been clinically validated. These data demonstrate the essentiality of the Dxr enzyme and its potential as a therapeutic target to combat *P. falciparum* malaria.

SUMMARY

An embodiment of the current invention relates to a method for treating or preventing a microbial infection in a subject that includes administering to the subject an effective amount of a composition or formulation that includes a small molecule having the structure of Formula (I):

or pharmaceutically acceptable salts and prodrugs thereof, where POM is $CH_2OC(=O)C(CH_3)_3$. In such embodiments, the microbial infection is caused by a eukaryotic pathogen, and the small molecule inhibits a function of an enzyme in a methylerythritol phosphate (MEP) pathway.

An embodiment of the invention relates to a method for inhibiting the growth of a eukaryotic pathogen that includes contacting said eukaryotic pathogen with an effective amount of a small molecule having the structure of Formula (I):

or pharmaceutically acceptable salts and prodrugs thereof, where POM is $CH_2OC(=O)C(CH_3)_3$. In such an embodiment, the small molecule inhibits a function of an enzyme in a methylerythritol phosphate (MEP) pathway.

An embodiment of the invention relates to a pharmaceutical composition that includes a small molecule having the structure of Formula (I):

or pharmaceutically acceptable salts and prodrugs thereof; and a pharmaceutically acceptable excipient, where POM is $CH_2OC(=O)C(CH_3)_3$. In such an embodiment, the small molecule interacts with a deoxyxylulose phosphate reductoisomerase (Dxr).

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Definitions

As used throughout the term "subject" refers to a mammal. In some cases, the mammal is human.

The term "in need thereof" refers to a subject infected with a microbial pathogen or at risk of becoming infected by the microbial pathogen. In some cases the microbial pathogen is a eukaryotic pathogen, and more specifically a eukaryotic pathogen belonging to the genus *Plasmodium*.

As used throughout the phrase an "effective amount" of a composition of the invention is measured by the therapeutic effectiveness of a compound of the invention, wherein at least one adverse effect of a disorder is ameliorated or alleviated. More specifically, administering a compound or composition results in complete or at least partial inhibition of a metabolic pathway or other biological processes in a pathogen. In addition, an effective amount is sufficient to result in at least some degree of alleviation or prevention of an infection caused by a pathogen, or prevention of an infection by the pathogen.

The terms "treating or preventing" are intended to include preventing, eradicating, or inhibiting the resulting increase of undesired physiological activity associated with a disorder or infection, for example, in the context of the therapeutic or prophylactic methods of the invention. In another embodiment, the term treating or preventing includes antagonistic effects, e.g., diminishment of the activity or production of mediators of a disorder.

As used herein and unless otherwise indicated, the term "formulation" refers to a composition comprising a compound of the invention that is described in a particular dosage form (e.g., tablet) or with a particular dosage amount (e.g., 30 mg/kg).

When administered to a subject (e.g., to an animal for veterinary use or to a human for clinical use), the compounds of the invention can be optionally administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 80% preferably at least 90%, more preferably at least 95%, and most preferably at least 99% of a compound of the invention by weight of the isolate.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, NO2, ONO, and ONO2 moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elselvier, N.Y. 1985).

The phrase "pharmaceutically acceptable excipient" may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Remington: The Science and Practice of Pharmacy, 21st Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropyl methylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In some embodiments, the described compositions are suitable for oral administration and may be presented as discrete units such as capsules, cachets, tablets, or lozenges, each containing a predetermined amount of the compound as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition described can be in the form of a pharmaceutical composition prepared as any appropriate unit dosage form. For example, the pharmaceutical compositions can be formulated for administration in solid or liquid form, including those adapted for the following: (1) oral administration, for example, as drenches, tablets (such as those targeted for buccal, sublingual and systemic absorption, including over-encapsulation tablets), capsules (such as hard, soft, dry-filled, liquid-filled, gelatin, non-gelatin or over-encapsulation capsules), caplets, boluses, powders, sachets, granules, pastes, mouth sprays, troches, lozenges, pellets, syrups, suspensions, elixirs, liquids, liposomes, emulsions and microemulsions; or (2) parenteral administration by, for example, subcutaneous, intramuscular, intravenous or epidural injection as, for example, a sterile solution or suspension. Additionally, the pharmaceutical compositions can be formulated for immediate, sustained, extended, delayed or controlled release.

In any of the methods provided herein, administration of the compound or pharmaceutical composition may be via any accepted mode known in the art, such as orally or parenterally. The term "parenterally" includes without limitation subcutaneously, intravenously, intramuscularly, intraperitoneally, intrathecally, intraventricularly, intrasternally, intracranially, by intraosseous injection and by infusion techniques. In one embodiment, the compound or pharmaceutical composition is administered orally. In another embodiment, the compound or pharmaceutical composition is administered parenterally. In another embodiment, the compound or pharmaceutical composition is administered intravenously. In another embodiment, the compound or pharmaceutical composition is administered intratumorally.

The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

An embodiment of the invention relates to a method for treating or preventing a microbial infection in a subject in need thereof that includes administering to the subject an effective amount of a composition or formulation that includes a small molecule having the structure of Formula (I):

or pharmaceutically acceptable salts and prodrugs thereof, where POM is $CH_2OC(=O)C(CH_3)_3$. In such embodiments, the microbial infection is caused by a eukaryotic pathogen, and the small molecule inhibits a function of an enzyme in a methylerythritol phosphate (MEP) pathway.

Some embodiments of the invention relate to the method above, where the infection is malaria.

Some embodiments of the invention relate to the method above, where the small molecule inhibits the function of the enzyme by binding to the enzyme.

Some embodiments of the invention relate to the method above, where the enzyme is Dxr.

Some embodiments of the invention relate to the method above, where the effective amount is between 25 mg/kg of body weight of the subject to 500 mg/kg of body weight of the subject.

Some embodiments of the invention relate to the method above, where the composition or formulation is administered to the subject as a single dose.

Some embodiments of the invention relate to the method above, where the composition or formulation is administered to the subject for at least 1 day.

Some embodiments of the invention relate to the method above, further including the step of administering to the subject an additional composition or formulation, where the additional composition or formulation treats the microbial infection or a secondary infection or a secondary symptom.

Some embodiments of the invention relate to the method above, where the additional composition or formulation includes a clinical agent selected from the list consisting of chloroquine, artemisinin, artesunate, artemether, lumafantrine, clindamycin, quinine, piperaquine, dihydroartemisinin, atovaquone, proguanil, doxycycline, tetracycline, primaquine, DSM-265 and KAE609.

An embodiment of the invention relates to a method for inhibiting the growth of a eukaryotic pathogen that includes contacting said eukaryotic pathogen with an effective amount of a small molecule having the structure of Formula (I):

or pharmaceutically acceptable salts and prodrugs thereof, where POM is $CH_2OC(=O)C(CH_3)_3$. In such an embodiment, the small molecule inhibits a function of an enzyme in a methylerythritol phosphate (MEP) pathway.

Some embodiments of the invention relate to the method above, where the eukaryotic pathogen belongs to the genus *Plasmodium*.

Some embodiments of the invention relate to the method above, where the small molecule inhibits the function of the enzyme by binding to the enzyme.

Some embodiments of the invention relate to the method above, where the enzyme is Dxr.

Some embodiments of the invention relate to the method above, further including the step of contacting the eukaryotic pathogen with an additional composition or formulation, wherein the additional composition inhibits a biological process of the eukaryotic pathogen.

Some embodiments of the invention relate to the method above, where the additional composition or formulation includes a clinical agent selected from the list consisting of chloroquine, artemisinin, artesunate, artemether, lumafantrine, clindamycin, quinine, piperaquine, dihydroartemisinin, atovaquone, proguanil, doxycycline, tetracycline, primaquine, DSM-265 and KAE609.

An embodiment of the invention relates to a pharmaceutical composition that includes a small molecule having the structure of Formula (I):

or pharmaceutically acceptable salts and prodrugs thereof; and a pharmaceutically acceptable excipient, where POM is $CH_2OC(=O)C(CH_3)_3$. In such an embodiment, the small molecule interacts with a deoxyxylulose phosphate reductoisomerase (Dxr).

In some embodiments, the methods, compounds and compositions described are used to prevent infection by a pathogen. In such embodiments, the methods, compounds and compositions are administered prophylactically to a subject either alone or in combination with another method, compound or composition for preventing or treating an infection by the same or a different pathogen.

Some embodiments relate to combination therapeutic approaches where any of the methods and/or compounds described are combined with at least one other therapeutic agent or method for treating malaria. Common therapeutic agents include, but are not limited to: chloroquine, artemisinin, artesunate, artemether, lumafantrine, clindamycin, quinine, piperaquine, dihydroartemisinin, atovaquone, proguanil, doxycycline, tetracycline, primaquine, DSM-265 and KAE609.

Example 1

RCB-185 is a Potent Inhibitor of Asexual *P. falciparum* Parasites

The most well-characterized antimalarial agent known to target Dxr is the phosphonic acid antibiotic fosmidomycin (FSM, FR-31564), which elicits its effect by substrate mimicry. Data indicate that FSM directly inhibits the *P. falciparum* Dxr enzyme with a half-maximal inhibitory concentration ($IC_{50}$) of 21-160 nM, and FSM is active against asexual *P. falciparum*. Since the MEP pathway is absent in mammals, FSM is safe with both a mouse and rat $LD_{50}$ of >11,000 mg/kg after oral administration. Similarly, FSM is well-tolerated in human patients with only mild to moderate adverse events reported.

Although the potency of FSM against whole parasites is low ($IC_{50}$=0.4 to 3.7 μM), parasite clearance is rapid with a mean of 44±18 h (mean±standard deviation). However, FSM demonstrates several poor pharmacokinetic properties, including a short serum half-life (1.87 h) and low bioavailability (20-40%) by oral dosing. In addition, a large number of patients treated with FSM in either monotherapy or in combination, suffer from recrudescent infections, likely due to subpar drug characteristics. Despite these shortcomings, FSM partnered with piperaquine is currently being evaluated in Phase II clinical trials as a non-artemisinin-based combination therapy to treat acute P. falciparum malaria.

To improve the potency and pharmacokinetics of FSM, while maintaining its inherent safety and efficacy, a series of prodrug analogs were synthesized that had lipophilic diesters on the phosphonate moiety of FSM (Jackson 2014). Since the compounds were fashioned to specifically target the Dxr enzyme of the MEP pathway, these analogs have been termed MEPicides. The most active compound was RCB-185, a pivaloyloxymethyl (POM)-protected, unsaturated analog of FSM.

RCB-185 has the following formula and chemical properties:

(I)

POM is $CH_2OC(=O)C(CH_3)_3$; and the molecular weight is 423.4 g/mol.

RCB-185 had low nM activity against blood-stage P. falciparum, and parasites treated with the MEPicide were chemically rescued by downstream isoprenoids. Metabolite analysis suggested that RCB-185 likely inhibits Dxr activity, as MEP metabolites downstream of the enzyme were depleted. Importantly, RCB-185 was highly active against drug-resistant P. falciparum, and the compound safely treated malaria-infected mice. Finally, computational studies predicted that RCB-185 exhibits a unique mode of binding to Dxr, which may account for its superior activity against P. falciparum when compared to FSM. Taken together, the data in this example demonstrate the antimalarial potential of RCB-185, and support further exploration of MEPicides as therapeutic agents.

MEPicides represent a novel series of therapeutic agents that inhibit enzymes of the MEP pathway, including the well-documented and clinically validated target, Dxr. Here we describe RCB-185, a lipophilic prodrug analog of fosmidomycin (FSM) that targets P. falciparum Dxr. RCB-185 is 50-fold more potent than FSM, lacks off-target effects, and safely cures malaria-infected mice. Since RCB-185 was synthesized via a unique chemical scaffold and existing therapies do not include MEP pathway targets, cross-resistance with frontline antimalarial agents is unlikely. The following data establish RCB-185 as a lead antimalarial compound against P. falciparum Dxr, and thus, should be subjected to additional preclinical testing.

Materials And Methods

P. falciparum Culture.

P. falciparum strains were obtained through the MR4 as part of the BEI Resources Repository, NIAID NIH (www.mr4.org): Plasmodium falciparum 3D7 (wild-type, WT), Plasmodium falciparum K1 (MRA-159; chloroquine and sulfadoxine-pyrimethamine resistant) deposited by D E Kyle, and Plasmodium falciparum IPC 5202 Battambang Cambodia 2011 (MRA-1240; chloroquine and artemisinin resistant) deposited by Didier Menard at the Institut Pasteur du Cambodge. The P. falciparum mutant containing increased levels of MEP pathway metabolites had1 (MRA-1257), and its compliment had1+PfHad1-GFP (MRA-1258), were generated in strain 3D7 as reported (BEI Resources; Guggisburg 2014). Parasites were cultured in a 2% suspension of human erythrocytes and RPMI 1640 (Sigma) medium supplemented with 27 mM sodium bicarbonate, 11 mM glucose, 5 mM HEPES, 1 mM sodium pyruvate, 0.37 mM hypoxanthine, 0.01 mM thymidine, 10 μg/ml gentamicin, and 0.5% albumax (Gibco) at 37° C., 5% $O_2$/5% $CO_2$/90% $N_2$ atmosphere as previously described (Zhang 2011).

P. falciparum Growth Inhibition Assays.

Asynchronous P. falciparum cultures were diluted to 1% parasitemia and were treated with FR900098 analogs at concentrations ranging from 0.25 ng/ml-100 μg/ml. Growth inhibition assays were performed in opaque 96-well plates at 100 μl culture volume. After 3 days, parasite growth was quantified by measuring DNA content using PicoGreen (Life Technologies), as described. Fluorescence was measured on a FLUOstar Omega microplate reader (BMG Labtech) at 485 nm excitation and 528 nm emission. Half maximal inhibitory concentration ($IC_{50}$) values were calculated by nonlinear regression analysis using GraphPad Prism software. For isopentenyl pyrophosphate (IPP) (Echelon) rescue experiments, 250 μM IPP was added to the appropriate wells for the duration of the experiment.

Sample Preparation for Mass Spectrometry Analysis.

P. falciparum strain 3D7 was cultured at 37° C. in 30 ml volumes in 100 mm tissue culture dishes (Techno Plastic Products) at 4% hematocrit until >8% parasitemia. Cultures were synchronized until >75% of parasites were in ring stage growth and then treated with RCB-185 at 1× or 7.5× the 3D7 $IC_{50}$ for 10 h. Cultures were then lysed with 5% saponin, the parasite pellets washed with 1× phosphate-buffered saline (PBS), and the pellets stored at −80° C. Samples were extracted via addition of 600 μl of ice-cold extraction solvent [chloroform, methanol, and acetonitrile (2:1:1, v/v/v)] and two liquid nitrogen-cooled 3.2 mm stainless steel beads, followed by homogenization in the TissueLyser II instrument (Qiagen, Valencia, Calif.) at 20 Hz for 5 min in a cold sample rack. Ice-cold water (600 μl) was added, and samples were homogenized for an additional 5 min at 20 Hz. After centrifugation (14,000 rcf at 4° C. for 5 min), the polar upper phase was aspirated and lyophilized. Dried samples were dissolved in 100 μl water and analyzed by LC-MS/MS.

LC-MS/MS analysis.

The 4000QTRAP LC-MS/MS system (AB Sciex) was used in multiple-reaction monitoring (MRM) mode using negative ionization. The detailed instrument configuration and compound-dependent parameters for isoprenoid precursors were as previously described (Zhang 2011). LC separation prior to MRM detection was achieved by ion pair reverse-phase chromatography as described previously, with 10 mM tributylammonium acetate (pH 5.1-5.5) used as the ion pair reagent and the following modifications: (1) RP-hydro 100 mm×2.0 mm, 2.5 μm high performance liquid chromatography column (Phenomenex), (2) flow rate of 0.14 ml/min, (3) solvent A of 10 mM tributylammonium acetate in 5% methanol, (4) binary LC gradient (20% solvent B (100% methanol) from 0 to 2.5 min, 30% B for 12.5 min, 80% B for 5 min, and column equilibration at for 5 min), and (5) autosampler injection volume of 20 μl. For DOXP and MEcPP metabolites, one-way ANOVA was used to test for significance (VassarStats). A t-test was used to test for significance between UNT and 1× RCB-185 CDP-ME levels (VassarStats). A significance test was not performed for MEP, as levels of the metabolite were below the limit of detection for RCB-185-treated parasites.

Gametocyte Assay

Cell Culture.

P. falciparum strain NF54 was grown in complete RPMI (RPMI 1640, 25 mM HEPES, 25 mM NaHCO (pH 7.3), 100 μg/ml hypoxanthine, and 5 μg/ml gentamicin (KD Biomedical, Columbia, Md.) supplemented with 10% human serum (Interstate Blood Bank, Memphis, Tenn.). Gametocyte cultures were set up at 0.2% parasitemia and 6% hematocrit. On the third day the hematocrit was reduced to 3% by increasing the media added during the daily feed. Following N-acetyl glucosamine (NAG, 50 mM) treatment on days 10-12 to eliminate asexual parasites, stage III/IV/V gametocytes were purified on a 65% Percoll gradient and returned to culture. The next day, the parasites were resuspended at 10% gametocytemia, and 2% hematocrit.

Drug Preparation.

A 96-well plate was prepared with 2× concentration of RCB-185 ranging 10 μM to 0.002 μM in complete RPMI with 1% DMSO as well as a positive control, 65 nM epoxomicin, and a negative control, 1% DMSO. Percoll purified NF54 strain P. falciparum gametocytes were added to individual wells at 2% hematocrit and 10% parasitemia in a 1:1 dilution, resulting in a final 1% hematocrit and a two-fold dilution of RCB-185 for a final concentration range of 5 μM to 0.001 μM and a final 0.5% DMSO, 32.5 nM epoxomicin. The plate was gassed with 90% $N_2$, 5% $O_2$, 5% $CO_2$ and incubated at 37° C. with compound for 72 h. Following incubation, cells were analyzed using flow cytomtetry as described below.

Flow Cytometry.

Cells were incubated at a final 0.1% hematocrit in 50 nM DiIC(1)5 with buffer containing 1.67 mg/ml glucose, 8 mg/mL NaCl, 8 mM Tris-Cl (pH 7.4) and incubated at 37° C. for 20-30 minutes prior to analysis on BD Accuri C6 flow cytometer. Uninfected RBCs and unstained P. falciparum infected RBCs were incubated with MitoProbe DiIC1(5) as controls to determine the threshold for MitoProbe DiIC1(5) (640 nm laser excitation and FL4 emission filter [675/25 nm]) positive, single, and intact cell populations. One-way ANOVA was used to test for significance between the three treatment groups (VassarStats).

Drug Testing Against Plasmodium berghei Asexual Blood Stages.

In vivo testing of RCB-185 against intraerythrocytic P. berghei parasites was performed by the Anti-Infectives Screening Core at NYU School of Medicine. Briefly, groups of 5-7 female Swiss Webster mice weighing 25-30 g were infected via intraperitoneal injection with $10^3$ transgenic P. berghei ANKA that express a fusion GFP (mutant 3) and firefly luciferase (LucIAV) fusion under the control of the constitutive eeflaα promoter that is stably integrated into the 230p locus (PbGFP-Luccon). Two days post-infection, mice were treated by intraperitoneal injection with 50 mg/kg of the test compound RCB-185 or 20 mg/kg chloroquine or 2% methyl cellulose, 0.5% tween-80 as positive and vehicle controls, respectively. Treatment continued once a day for 5 days. At 7 days post-infection, mice were administered 2.5% isofluorane via a nose cone, and once anesthesized, were injected i.p. with 150 mg/kg of D-Luciferin Potassium-salt (Goldbio) dissolved in PBS. Mice were imaged 5-10 min after injection of luciferin with an IVIS 100 (Xenogen, Alameda, Calif.) and data acquisition and analysis were performed with Livinglmage (Xenogen) to quantify the level of infection. To test for significance between vehicle- and RCB-185-treated mice, a t-test was used (VassarStats).

Results

Figure 1:
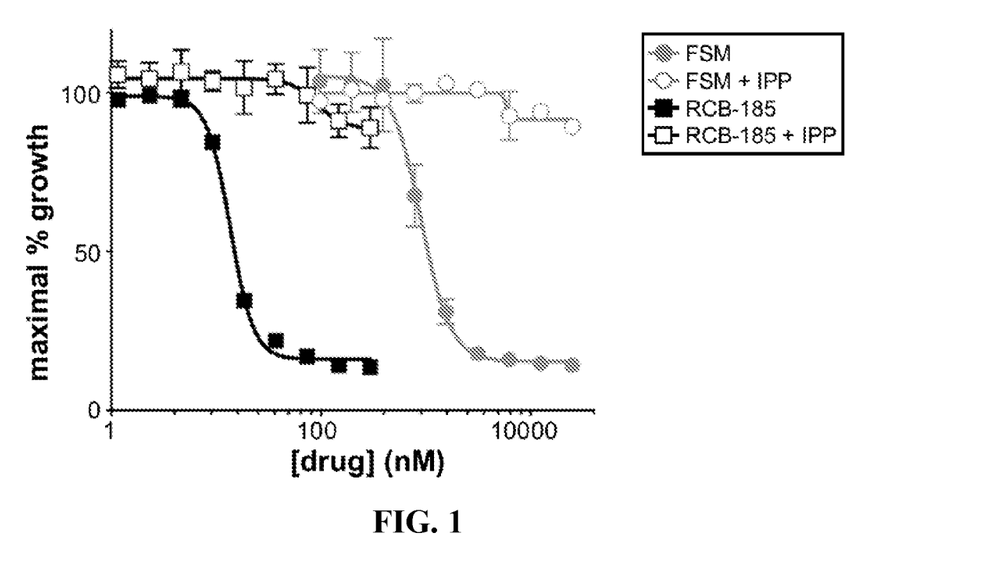
FIG. 1 is a graph of *P. falciparum* strain 3D7 treated with FSM (grey circles) or RCB-185 (black squares) at a range of concentrations and growth quantified after 72 h.

To evaluate the activity of RCB-185 against blood stage parasites, asynchronous cultures of P. falciparum strain 3D7 were treated with RCB-185 and then growth was quantified after 72 h as described. Data indicate that RCB-185 has a mean $IC_{50}$=18.3±1.9 nM against asexual parasites (FIG. 1 and Table 1). For comparison, the in vitro potency of RCB-185 is similar to the first-line antimalarial agent artemisinin, which has an $IC_{50}$=10.4±1.6 nM against 3D7 parasites (mean±SEM from >3 independent experiments). Furthermore, RCB-185 has a 50-fold lower $IC_{50}$ value than the well-described Dxr inhibitor fosmidomycin (FSM), which has an $IC_{50}$ value of 1021.5±77.8 nM (Table 1). These data indicate that RCB-185 is a robust inhibitor of parasite growth, and as such, requires additional characterization.

TABLE 1

RCB-185 is active against multi-drug resistant P. falciparum

| Cell line | FSM $IC_{50}$ (nM) | RCB-185 $IC_{50}$ (nM) |
| --- | --- | --- |
| P. falciparum 3D7 (pan-sensitive, lab adapted) | 1021.5 ± 77.8 | 18.3 ± 1.9 |
| P. falciparum 7G8 (quinine, chloroquine, and pyrimethamine resistant) | 1235.7 ± 188.7 | 46.7 ± 10.9 |
| P. falciparum D6 (mefloquine resistant) | 1339.5 ± 246.7 | 37.6 ± 10.0 |
| P. falciparum D10 (mefloquine resistant) | 2184.0 ± 353.0 | 42.5 ± 11.5 |
| P. falciparum K1 (chloroquine and sulfadoxine-pyrimethamine resistant) | 837.0 ± 141.0 | 31.9 ± 1.0 |
| P. falciparum Battambang (chloroquine and artemisinin resistant) | 862.8 ± 247.5 | 21.1 ± 1.8 |
| Human HepG2 cells | n.d. | >100,000 |

FIG. 1 shows a graph of P. falciparum strain 3D7 treated with FSM (grey circles) or RCB-185 (black squares) at a range of concentrations and growth quantified by PicoGreen (Life Technologies) after 72 h. The downstream isoprenoid precursor IPP rescues both FSM and RCB-185-treated parasites (open shapes) indicating the compound is a specific inhibitor of the MEP pathway in P. falciparum. Shown is a representative graph from 3 or more independent experiments. Also displayed are the $IC_{50}$ values (mean±SEM) for FSM and RCB-185 from >10 independent experiments.

RCB-185 Inhibits Isoprenoid Biosynthesis in P. falciparum.

Malaria parasites treated with small molecules that specifically target apicoplast functions, including compounds that block MEP pathway enzymes, are chemically rescued if cultures are supplemented with the isoprenoid precursor IPP (Imlay 2015). To investigate whether the loss in viability caused by RCB-185 is reversed by IPP supplementation, P. falciparum was treated with RCB-185 over a range of concentrations (1.2 nM-590.5 nM) and then evaluated whether IPP could rescue growth. As displayed in FIG. 1, 250 μM IPP supports growth of P. falciparum treated with RCB-185 at all concentrations tested. These data are similar to the reverse in growth inhibition observed in FSM-treated parasites supplemented with IPP (FIG. 1).

Figure 2:
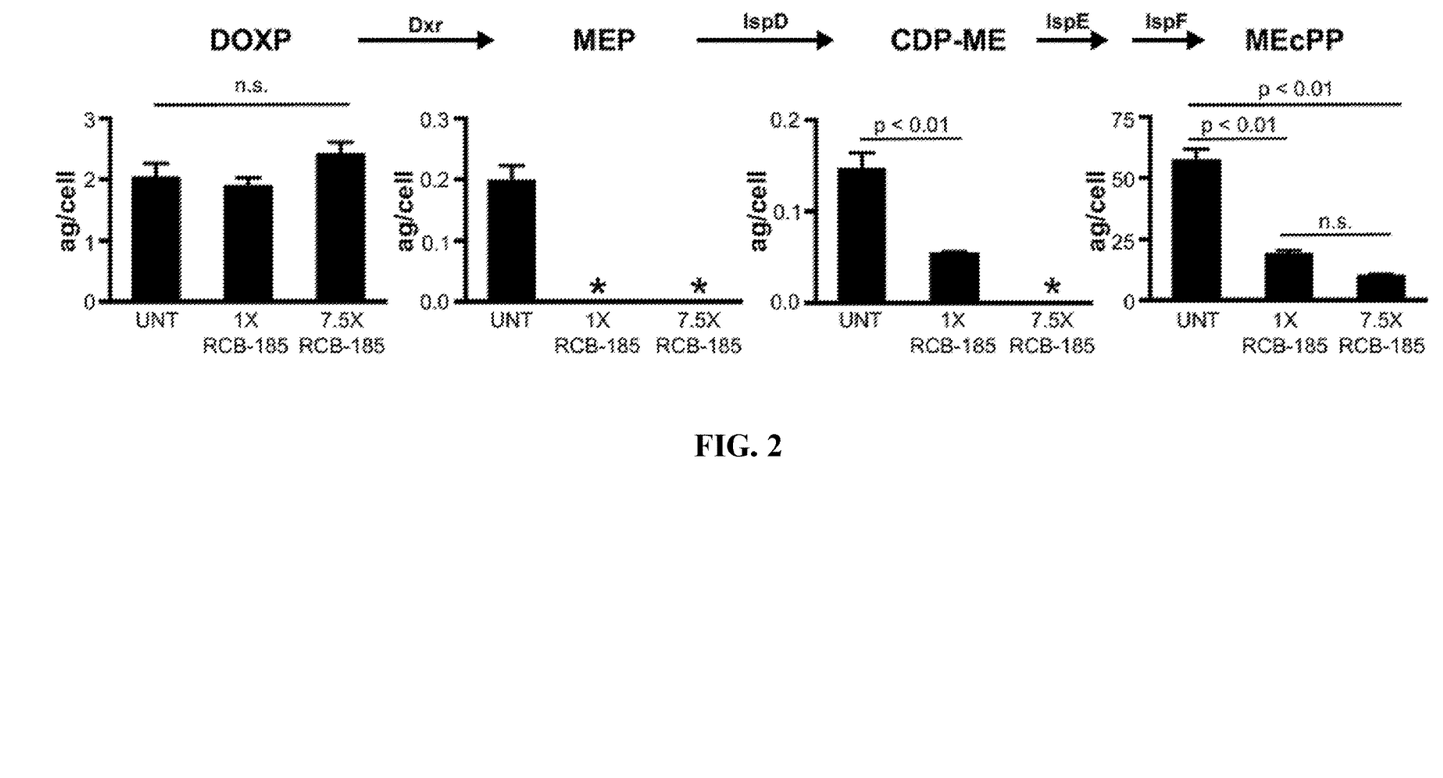
FIG. 2 shows bar graphs of RCB-185 inhibition of the MEP pathway in *P. falciparum*.

The chemical rescue of RCB-185-treated parasites indicates the compound affects an apicoplast function, and strongly implicates isoprenoid biosynthesis as the target. As RCB-185 is an analog of FSM, it was predicted that treatment of P. falciparum with the MEPicide would deplete pathway intermediates beyond its proposed target, Dxr. To directly quantify MEP metabolites from treated parasites, a liquid chromatography-mass spectrometry method that measures cellular levels of key MEP pathway intermediates, including 1-deoxy-D-xylulose 5-phosphate (DOXP), 2-C-methylerythritol 4-phosphate (MEP), 4-diphosphocytidyl-2-C-methylerythritol (CDP-ME) and 2-C-methyl-D-erythritol 2,4-cyclopyrophosphate (MEcPP) (Zhang 2011) was employed. Briefly, 3D7 parasites were treated +/−RCB-185 for 10 h and MEP pathway metabolites measured by LC-MS/MS. As anticipated, the metabolic profiling data indicated there was no significant difference (denoted by n.s.) in the levels of DOXP, the substrate for P. falciparum Dxr, in RCB-185-treated cultures (FIG. 2). However, MEP pathway intermediates measured downstream of Dxr were greatly diminished in treated parasites. Both MEP and CDP-ME were below the limits of detection (asterisks; 12.5 ng/ml and 1.25 ng/mL, respectively; Zhang 2011), and levels of the most distal metabolite MEcPP were significantly reduced when compared to untreated parasites (p<0.01) (FIG. 2). Specifically, P. falciparum treated with RCB-185 at 1× and 7.5× the $IC_{50}$ value of 18.3 nM corresponded to 3.0- and 5.7-fold reductions in MEcPP levels, respectively. Our metabolic data strongly suggest that RCB-185 inhibits the first committed step of isoprenoid biosynthesis through direct inhibition of Dxr.

FIG. 2 shows four bar graphs of RCB-185 inhibition of the MEP pathway in P. falciparum. MEP pathway metabolites were compared between untreated (UNT) P. falciparum and parasites treated with RCB-185 at either 1× or 7.5× the WT $IC_{50}$ value of 18.3 nM. After 10 h treatment, cultures were saponin-lysed and the pellets analyzed by LC-MS/MS. Displayed are the means±SEM of the metabolite levels from three independent experiments. Asterisks denote metabolites that were below the limit of detection.

Figure 3:
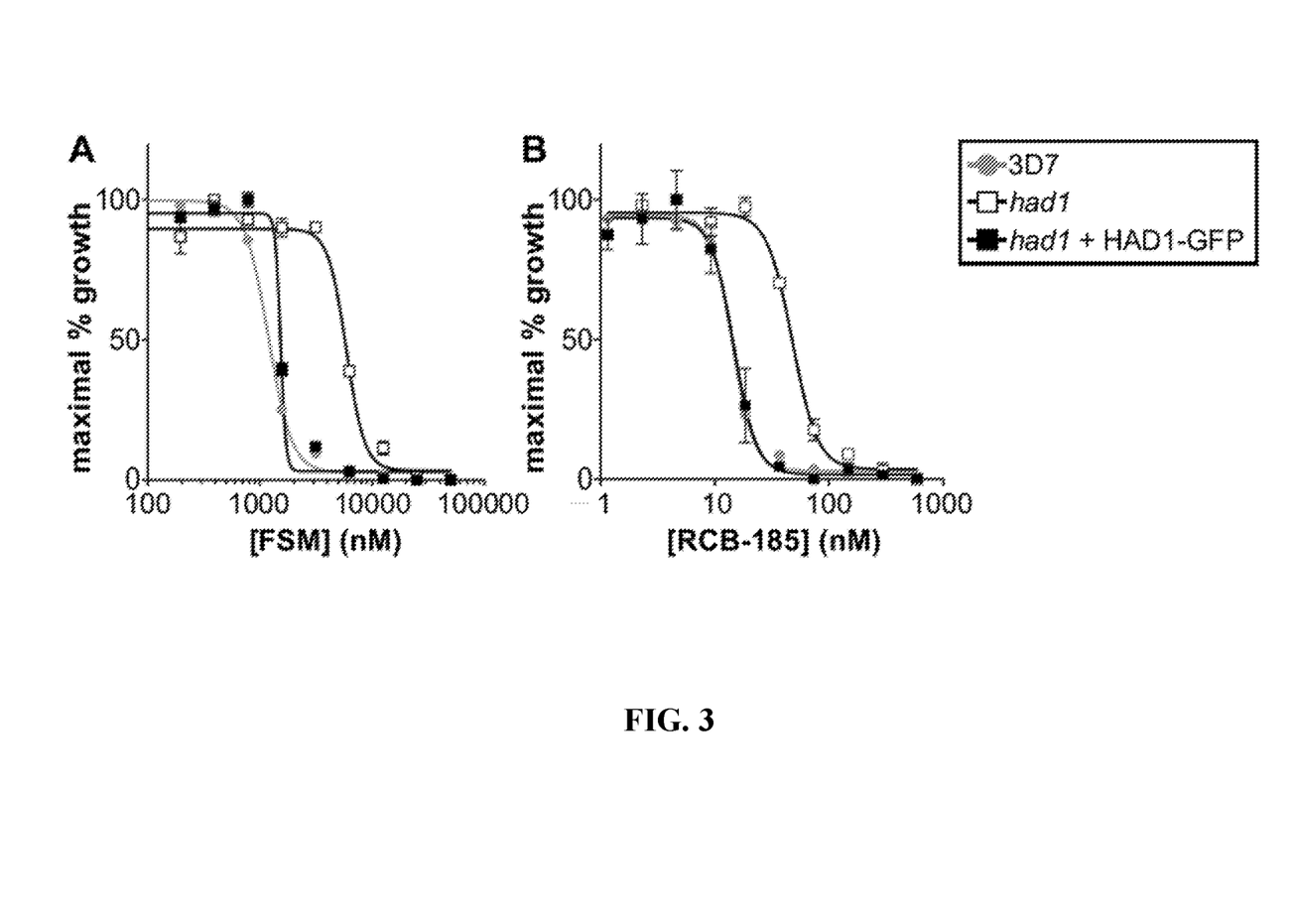
FIG. 3 shows graphs comparing Fosmidomycin resistance with RCB-185 resistance.

To further interrogate the whether RCB-185 inhibits the MEP pathway, its activity against a P. falciparum strain that produces high levels of the Dxr substrate, DOXP, due to a mutation in the sugar phosphatase had1 (PF3D7_1033400) was tested. Previous data indicate that an increase in the intracellular pool of DOXP impedes the competitive inhibition of Dxr by FSM, which results in FSM-resistant parasites (Guggisberg 2014). It was predicted that a surplus in cellular DOXP would promote RCB-185 resistance by a mechanism analogous to the FSM resistance displayed by had1 parasites (FIG. 3, panel A; Guggisberg 2014). Indeed, had1 parasites were 3.8-fold more resistant to RCB-185 with an $IC_{50}$=76.5±18.5 nM when compared to an $IC_{50}$=19.9±4.2 nM for WT parasites (p<0.05, FIG. 3, panel B). Importantly, RCB-185 sensitivity was restored if a WT copy of had1 was supplied in the mutant strain ($IC_{50}$=26.0±6.4; FIG. 3 panel B). These data indicate that similar to FSM, RCB-185 may compete with DOXP. Collectively, the data demonstrate that RCB-185 is a potent inhibitor of P. falciparum growth through inhibition of Dxr in the isoprenoid biosynthetic pathway.

FIG. 3 shows graphs comparing FSM resistance with RCB-185 resistance. Dose-dependent growth inhibition by FSM (FIG. 3 panel A) or RCB-185 (FIG. 3 panel B) was determined for the parental strain (3D7; closed circles, grey line), the fosmidomycin-resistant PfHad1 loss-of-function parasite strain (had1; open squares, black line), and the FSM-sensitive complemented strain (had1+HAD1-GFP; closed squares, black line). For FSM, the parent strain has an $IC_{50}$=1162.0±157.9 nM, while had1 has an $IC_{50}$=5348.1±830.6 nM. For RCB-185, the parent strain has an $IC_{50}$=19.9±4.2 nM, while had1 has an $IC_{50}$=76.5±18.5 nM. Data (mean±SEM) are representative of at least three independent biological replicates performed in duplicate.

RCB-185 is Active Against Drug-Resistant P. falciparum.

A major threat to public health is the emergence of P. falciparum resistance to current therapies, including the frontline agents artemisinin and its derivatives artesunate and artemether. Thus, the discovery and development of new classes of antibiotics that effectively treat drug-resistant parasites is essential. To assess whether RCB-185 could inhibit growth of resistant parasites, environmental strains of P. falciparum that were resistant to chloroquine, sulfadoxine/pyrimethamine, and/or artemisinin we obtained and tested. The isolates were treated with RCB-185 for 72 h and growth inhibition quantified as described. As displayed in Table 1, the resistant strains were sensitive to RCB-185 and the $IC_{50}$ values were not significantly different than WT (3D7) parasites. These data demonstrate the utility of MEPicides in combating drug-resistance.

RCB-185 is Potent, Safe, and Efficacious in a Mouse Model of Malaria.

Figure 4:
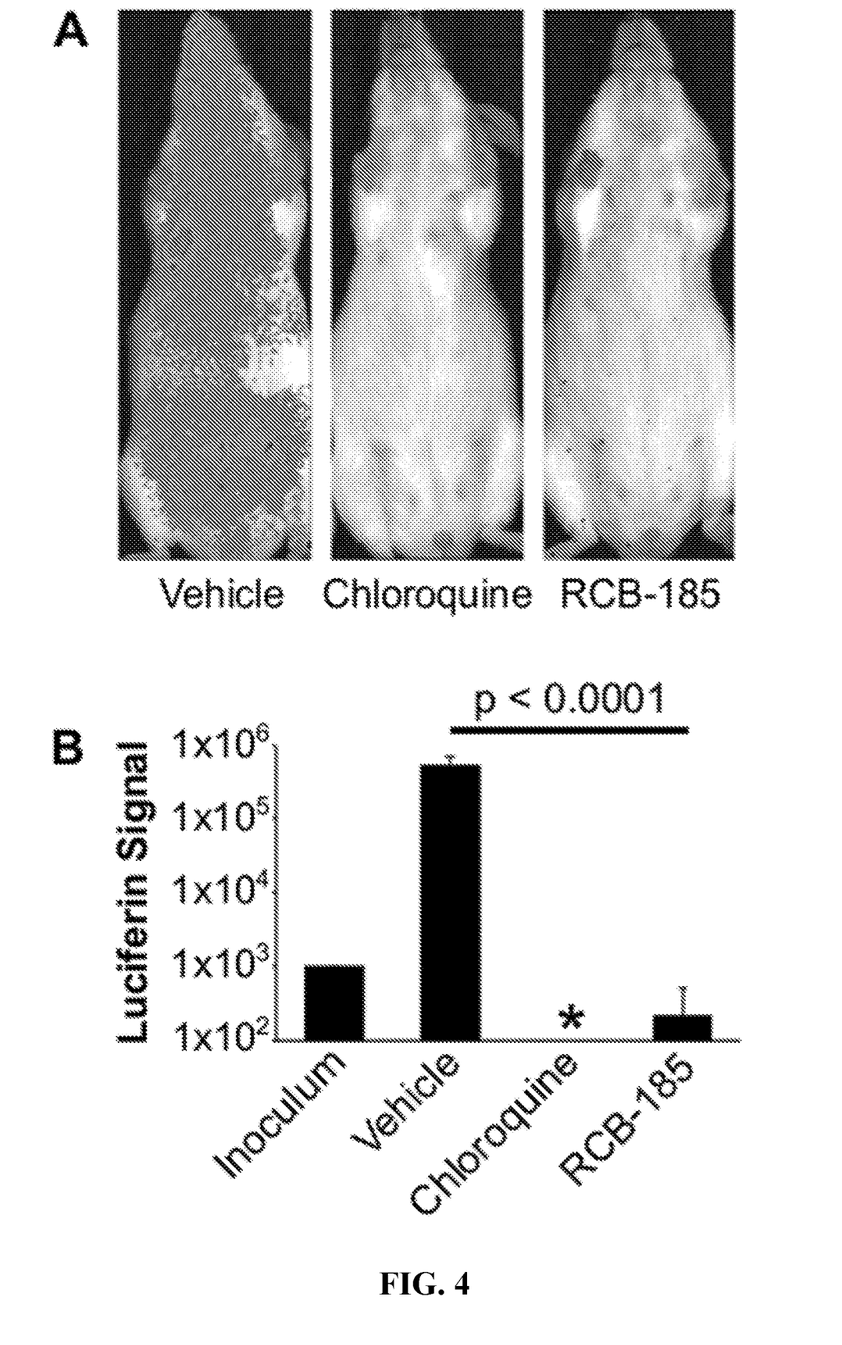
FIG. 4 is an image and related graph showing that RCB-185 is efficacious in a mouse model of malaria.

Due to the pronounced activity of RCB-185 against P. falciparum in vitro, it was tested whether the compound could effectively treat asexual blood stages in a mouse model of malaria. Briefly, groups of female Swiss Webster mice were infected by intraperitoneal injection with $10^3$ blood-stage P. berghei ANKA expressing luciferase. Mice were dosed once per day with vehicle, 20 mg/kg chloroquine, or 50 mg/kg RCB-185, and the parasite burden quantified by measuring luciferase signal intensity at 7 days post-infection. As demonstrated by the vehicle control, the number of P. berghei expands several log after one week of infection (FIG. 4). Mice administered the control therapeutic chloroquine were successfully cleared of infection, as the luciferase signal was below the limit of detection (designated by an asterisk). Notably, P. berghei-infected mice treated with RCB-185 had more than a 3-log drop in the parasite load when compared to the vehicle (p<0.0001; FIG. 4). In addition, no adverse effects were observed in mice administered the MEPicide suggesting the compound was well tolerated at the treatment concentration. These data corroborate previous work that found RCB-185 is nontoxic to human cell lines (Table 1; Hep2G cells >100,000 nM), and further, supports its value as an antimalarial agent.

FIG. 4 is an image and related graph showing that RCB-185 is efficacious in a mouse model of malaria. Groups of 5-7 Swiss Webster mice were infected with $10^3$ P. berghei ANKA expressing luciferase via intraperitoneal injection. On days 2-7, mice were dosed once per day with vehicle, 20 mg/kg chloroquine, or 50 mg/kg RCB-185. At 7 days post-infection, mice were imaged with an IVIS imager and the parasite burden quantified by luciferase signal intensity. Representative images are shown for each treatment condition (top), and the average luciferase signal intensity quantified for each treatment (bottom). Displayed are the means±SD for each treatment group. The asterisk indicates the luciferase signal was below the limit of detection.

Discussion

Similar to FSM, it is suspected that the failure of RCB-185 to kill gametocytes may be a defect in import or alternatively, may suggest that a reservoir of essential isoprenoids exist within the gametocyte apicoplast that precludes its effect on de novo isoprenoid biosynthesis (Bowman 2014).

Example 2

1) In vivo efficacy in the human erythrocyte-engrafted SCID mouse model: Results from this assay would establish in vivo efficacy of this compound.

2) In vivo pharmacokinetic (PK) parameters. Measure serum half-life (of the prodrug and active component).

3) In vivo efficacy in liver stage model. This data will show the breadth of in vivo activity of this compound.

It should be understood that various alternatives to the embodiments of the invention described herein may be employed in practicing the invention. It is intended that the scope of the invention, methods and structures within the scope of the invention includes equivalents.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

Guggisberg A M, Park J, Edwards R L, Kelly M L, Hodge D M, Tolia N H, Odom A R (2014) A sugar phosphatase regulates the methylerythritol phosphate (MEP) pathway in malaria parasites. *Nat Commun* 5:4467.

Imlay L S, Odom A R (2014) Isoprenoid metabolism in apicomplexan parasites. *Curr Clin Microbiol Rep* 1(3-4): 37-50.

Imlay L S, Armstrong C M, Masters M C, Li T, Price K E, Edwards R L, Mann K M, Li L X, Stallings C L, Berry N G, O'Neill P M, Odom A R (2015) *Plasmodium* IspD (2-C-Methyl-d-erythritol 4-Phosphate Cytidyltransferase), an Essential and Druggable Antimalarial Target. *ACS Infect Dis* 1(4): 157-167.

Jackson E R, San Jose G, Brothers R C, Edelstein E K, Sheldon Z Haymond A, Johny C, Boshoff H I, Couch R D, Dowd C S (2014) The effect of chain length and unsaturation on Mtb Dxr inhibition and antitubercular killing activity of FR900098 analogs. *Bioorg Med Chem Lett* 24(2): 649-653.

Jackson E R and Dowd C S (2012) Inhibition of 1-Deoxy-D-xylulose-5-phosphate reductoisomerase (Dxr): a review of the synthesis and biological evaluation of recent inhibitors. *Curr Top Med Chem* 12(7): 706-728.

Zhang B, Watts K M, Hodge D, Kemp L M, Hunstad D A, Hicks L M, Odom A R. (2011) A second target of the antimalarial and antibacterial agent fosmidomycin revealed by cellular metabolic profiling. *Biochemistry*. 50(17): 3570-3577.

We claim:

1. A method for treating or preventing a microbial infection caused by a eukaryotic pathogen belonging to the genus *Plasmodium* in a subject in need thereof comprising administering to the subject an effective amount of a composition or formulation comprising a small molecule having the structure of Formula (I):

or pharmaceutically acceptable salts and prodrugs thereof, where POM is $CH_2OC(=O)C(CH_3)_3$, and wherein the small molecule inhibits a function of an enzyme in a methylerythritol phosphate (MEP) pathway.

2. The method of claim 1, wherein the infection is malaria.

3. The method of claim 1, wherein the small molecule inhibits the function of the enzyme by binding to the enzyme.

4. The method of claim 1, wherein the enzyme is Dxr.

5. The method of claim 1, wherein the effective amount is between 25 mg/kg of body weight of the subject to 500 mg/kg of body weight of the subject.

6. The method of claim 1, wherein the composition or formulation is administered to the subject as a single dose.

7. The method of claim 1, wherein the composition or formulation is administered to the subject for at least 1 day.

8. The method of claim 1, further comprising administering to the subject an additional composition or formulation, wherein the additional composition or formulation treats the microbial infection or a secondary infection or a secondary symptom.

9. The method of claim 1, wherein the additional composition or formulation comprises a clinical agent selected from the list consisting of chloroquine, artemisinin, artesunate, artemether, lumafantrine, clindamycin, quinine, piperaquine, dihydroartemisinin, atovaquone, proguanil, doxycycline, tetracycline, primaquine, DSM-265 and KAE609.

10. A method for inhibiting the growth of a eukaryotic pathogen belonging to the genus *Plasmodium* comprising contacting said eukaryotic pathogen with an effective amount of a small molecule having the structure of Formula (I):

or pharmaceutically acceptable salts and prodrugs thereof, where POM is $CH_2OC(=O)C(CH_3)_3$, and wherein the small molecule inhibits a function of an enzyme in a methylerythritol phosphate (MEP) pathway.

11. The method of claim 10, wherein the small molecule inhibits the function of the enzyme by binding to the enzyme.

12. The method of claim 10, wherein the enzyme is Dxr.

13. The method of claim 10, further comprising contacting the eukaryotic pathogen with an additional composition or formulation, wherein the additional composition inhibits a biological process of the eukaryotic pathogen.

14. The method of claim 13, wherein the additional composition or formulation comprises a clinical agent selected from the list consisting of chloroquine, artemisinin, artesunate, artemether, lumafantrine, clindamycin, quinine, piperaquine, dihydroartemisinin, atovaquone, proguanil, doxycycline, tetracycline, primaquine, DS M-265 and KAE609.

\* \* \* \* \*